(12) United States Patent
Millón Peñuela et al.

(10) Patent No.: US 11,986,513 B2
(45) Date of Patent: May 21, 2024

(54) GAL(1-15) AND ANALOGUES THEREOF FOR USE IN THE PREVENTION AND/OR TREATMENT OF ALCOHOL-RELATED EFFECTS AND DISORDERS

(71) Applicant: UNIVERSIDAD DE MÁLAGA, Málaga (ES)

(72) Inventors: Carmelo Millón Peñuela, Málaga (ES); Antonio Flores Burgess, Málaga (ES); Belén Gago Calderón, Málaga (ES); María Inmaculada García Fernandez, Málaga (ES); JoséÁngel Narváez Bueno, Málaga (ES); Luis Javier Santín Núñez, Málaga (ES); Mª Zaida Díaz Cabiale, Málaga (ES)

(73) Assignee: UNIVERSIDAD DE MÁLAGA, Málaga (ES)

( * ) Notice: Subject to any disclaimer, the term of this patent is extended or adjusted under 35 U.S.C. 154(b) by 886 days.

(21) Appl. No.: 16/757,706

(22) PCT Filed: Oct. 2, 2018

(86) PCT No.: PCT/ES2018/070634
§ 371 (c)(1),
(2) Date: Apr. 20, 2020

(87) PCT Pub. No.: WO2019/068948
PCT Pub. Date: Apr. 11, 2019

(65) Prior Publication Data
US 2023/0158115 A1    May 25, 2023

(30) Foreign Application Priority Data
Oct. 2, 2017  (ES) .............................. ES201731170

(51) Int. Cl.
*A61K 38/22* (2006.01)
*A61K 38/10* (2006.01)
*A61P 39/02* (2006.01)

(52) U.S. Cl.
CPC .............. *A61K 38/22* (2013.01); *A61P 39/02* (2018.01)

(58) Field of Classification Search
CPC .......... A61K 38/22; A61K 38/10; A61P 39/02
See application file for complete search history.

(56) References Cited

U.S. PATENT DOCUMENTS

2020/0055808 A1    2/2020    Montañez Vega et al.

FOREIGN PATENT DOCUMENTS

WO    2005/080427 A1    9/2005

OTHER PUBLICATIONS

Olkowicz et al., "New GALANIN(1-15) Analogues Modified in Positions 9, 10 and 11 Act as Galanin Antagonists on Glucose-Induced Insulin Secretion," Journal of Physiology and Pharmacology, 2007, 58(4): 859-872. (Year: 2007).*
Przewlocka et al., "Intracerebroventricular galanin and N-terminal galanin fragment enhance the morphine-induced analgesia in the rat," J. Neural Transm [Gen Sect], 1995, 102: 229-235. (Year: 1995).*
Alcohol use disorder from Mayo Clinic, pp. 1-16. Accessed Jul. 25, 2023. (Year: 2023).*
Ash et al., "Galanin-3 Receptor Antagonism by SNAP 37889 Reduces Motivation to Self-administer Alcohol and Attenuates Cue-Induced Reinstatement of Alcohol-Seeking in iP Rats," *J Pharmacol Sci* 125:211-216, 2014.
Ash et al., "The galanin-3 receptor antagonist, SNAP 37889, reduces operant responding for ethanol in alcohol-preferring rats," *Regulatory Peptides* 166:59-67, 2011.
Belfer et al., "Alcoholism is associated with GALR3 but not two other galnin receptor genes," *Genes, Brain and Behavior* 6:473-481, 2007.
Borroto-Escuela et al., "Fibroblast Growth Factor Receptor 1-5-Hydroxytryptamine 1A Heteroreceptor Complexes and Their Enhancement of Hippocampal Plasticity," *Biol Psychiatry* 71:84-91, 2012.
Brabant et al., "Stimulant and motivational effects of alcohol: Lessons from rodent and primate models," *Pharmacology, Biochemistry and Behavior* 122:37-52, 2014.
Branchek et al., "Galanin receptor subtypes," *TiPS* 21:109-117, 2000.
Díaz-Cabiale et al., "Galanin receptor/Neuropeptide Y receptor interactions in the dorsal raphe nucleus of the rat," *Neuropharmacology* 61:80-86, 2011.
Díaz-Cabiale et al., "Galanin-(1-16) modulates 5-HT1A receptors in the ventral limbic cortex of the rat," *Nuerochemistry* 11(3):515-519, 2000.
Díaz-Cabiale et al., "Neurochemical Modulation of Central Cardiovascular Control: The Integrative Role of Galanin," *Galanin, Experientia Supplementum* 102:113-131, 2010.
Díaz-Cabiale et al., "Role of galanin and galanin(1-15) on central cardiovascular control," *Neuropeptides* 39:185-190, 2005.
Flores-Burgess et al., "Galanin (1-15) enhancement of the behavioral effects of Fluoxetine in the forced swimming test gives a new therapeutic stragegy against depression," *Neuropharmacology* 118:233-241, 2017.
Fuxe et al., "On the existence and function of galanin receptor heteromers in the central nervous system," *Frontiers in Endocrinology | Neuroendocrine Science* 3(127):Jan. 12, 2012.

(Continued)

Primary Examiner — Julie Ha
(74) Attorney, Agent, or Firm — Seed IP Law Group LLP

(57) ABSTRACT

GAL(1-15) and analogues thereof for use in the prevention and/or treatment of alcohol-related effects and disorders. The present invention relates to the use of galanin(1-15), which has the general formula Gly-Trp-Thr-Leu-Asn-Ser-Ala-Gly-Tyr-Leu-Leu-Gly-Pro-His-Ala (GWTLNSAGYLLGPHA)(SEQ ID NO: 1), or an analogue thereof, or pharmaceutically acceptable salt, ester, tautomer, solvate, or hydrate thereof, or a pharmaceutical composition or kit comprising any of same, for use in the prevention and/or treatment of alcohol-related effects and disorders, especially the use thereof to reduce alcohol consumption.

5 Claims, 8 Drawing Sheets

Specification includes a Sequence Listing.

(56) References Cited

OTHER PUBLICATIONS

Fuxe et al., "Receptor-receptor interactions within receptor mosaics. Impact on neuropsychopharmacology," *Brain Research Reviews* 58:415-452, 2008.
Gomez et al., "Differential effects of ghrelin antagonists on alcohol drinking and reinforcement in mouse and rat models of alcohol dependence," *Neuropharmacology* 97:182-193, 2015.
Green et al., "Ethanol drinking in rodents: is free-choice drinking related to the reinforcing effects of ethanol," *Alcohol* 42:Jan. 11, 2008.
Hedlund et al., "Evidence for specific N-terminal galanin fragment binding sites in the rat brain," *European Journal of Pharmacology* 224:203-205, 1992.
Hedlund et al., "Galanin and 5-HT$_{1A}$ Receptor Interactions as an Integrative Mechanism in 5-HT Neurotransmission in the Brain," *Annals New York Academy of Science* 780:193-212, 1996.
Hedlund et al., "Galanin-(1-15), but not galanin-(1-29), modulates 5-HT$_{1A}$ receptors in the dorsal hippocampus of the rat brain: possible existence of galanin receptors subtypes," *Brain Research* 634:163-167, 1994.
Jacobowitz et al., "Galanin in the brain: chemoarchitectonics and brain cartography—a historical review," *Peptides* 25:433-464, 2004.
Karatayev et al., "Galanin Knockout Mice Show Disturbances in Ethanol Consumption and Expression of Hypothalamic Peptides That Stimulate Ethanol Intake," *Alcoholism: Clinical and Experimental Research* 34(1):72-80, 2010.
Karatayev et al., "Increased Intake of Ethanol and Dietary Fat in Galanin Overexpressing Mice," *Alcohol* 43(8):571-580, 2009 (NIH Public Access Author Manuscript, available in PMC Dec. 21, 2009)(16 pages).
Koob, "Drugs of abuse: anatomy, pharmacology and function of reward pathways," *TiPS* 13:177-184, 1992.
Lang et al., "Physiology, Signaling, and Pharmacology of Galanin Peptides and Receptors: Three Decades of Emerging Diversity," *Pharmacol Rev* 67:118-175, 2015.
Leeman et al., "Ethanol Consumption: How Should We Measure It? Achieving Consilience between Human and Animal Phenotypes," *Addict Biol.* 15(2):109-124, 2010 (NIH Public Access Author Manuscript, available in PMC Apr. 1, 2011)(23 pages).
Leibowitz et al., "Ethanol intake increases galanin mRNA in the hypothalamus and withdrawal decreases it," *Physiology & Behavior* 79:103-111, 2003.
Lewis et al., "Galanin and alcohol dependence: Neurobehavioral research," *Neuropeptides* 39:317-321, 2005.
Lewis et al., "Galanin Microinjection in the Third Ventricle Increases Voluntary Ethanol Intake," *Alcoholism: Clinical and Experimental Research* 28(12):1822-1828, 2004.
Millón et al., "A Role for Galanin N-Terminal Fragment (1-15) in Anxiety- and Depression-Related Behaviors in Rats," *International Journal of Neuropsychopharmacy* 18:Jan. 13, 2015.
Millón et al., "Galanin (1-15) enhances the antidepressant effects of the 5-HT1A receptor agonist 8-OH-DPAT: involvement of the raphe-hippocampal 5-HT neuron system," *Brain Struct Funct*: 2016 (14 pages).
Millón et al., "The neuropeptides Galanin and Galanin (1-15) in depression-like behaviours," *Neuropeptides* 64:39-45, 2017.
Mitsukawa et al., "Galanin, galanin receptors and drug targets," *Cell. Mol. Life Sci.* 65:1796-1805, 2008.
Picciotto et al., "Effects of galanin on monoaminergic systems and HPA axis: potential mechanisms underlying the effects of galanin on addiction- and stress-related behaviors," *Brain Res.* 1314C:206, 2010 (NIH Public Access Author Manuscript, available in PMC Feb. 16, 2011)(23 pages).
Picciotto, "Galanin and addiction," *Cell. Mol. Life Sci.*: Jan. 8, 2008.
Pierce et al., "The mesolimbic dopamine system: The final common pathway for the reinforcing effect of drug of abuse?" *Neuroscience and Biobehavioral Reviews* 30:215-238, 2006.
Rada et al., "Ethanol intake is increased by injection of galanin in the paraventricular nucleus and reduced by a galanin antagonist," *Alcohol* 33:91-97, 2004.
Rada et al., "Galanin in the hypothalamus raises dopamine and lowers acetylcholine release in the nucleus accumbens: a possible mechanism for hypothalamic initiation of feeding behavior," *Brain Research* 798:Jan. 6, 1998.
Scheller et al., "The galanin-3 receptor antagonist, SNAP 37889, suppresses alcohol drinking and morphine self-administration in mice," *Neuropharmacy* 118:Jan. 12, 2017.
Schneider et al., "Orexigenic Peptides and Alcohol Intake: Differential Effects of Orexin, Galanin, and Ghrelin," *Alcoholism: Clinical and Experimental Research* 31(11):1858-1865, 2007.
Simms et al., "Intermittent Access to 20% Ethanol Induces High Ethanol Consumption in Long-Evans and Wistar Rats," *Alcohol Clin Exp Res* 32(10):1816-1823, 2008 (NIH Public Access Author Manuscript, available in PMC Aug. 6, 2011)(15 pages).
Smith et al., "Cloned Human and Rat Galanin GALR3 Receptors," *The Journal of Biological Chemistry* 273(36):23321-23326, 1998 (7 pages).
Tarragón et al., "Ethanol drinking-in-the-dark facilitates behavioral sensitization to ethanol in C57BL/6J, BALB/cByJ, but not in mu-opioid receptor deficient CXBK mice," *Pharmacology, Biochemistry and Behavior* 101:14-23, 2012.
Tatemoto et al., "Galanin—a novel biologically active peptide from porcine intestine," *FEBS* 1012 164(1):124-128, 1983.
Tsuda et al., "Effects of Galanin on Dopamine Release in the Central Nervous System of Normotensive and Spontaneously Hypertensive Rats," *AJH* 11:1475-1479, 1998.
Vallöf et al., "Central administration of the anorexigenic peptide neuromedin U decreases alcohol intake and attenuates alcohol-induced reward in rodents," *Addiction Biology* 22:640-651, 2016.
Waters et al., "Distribution of Galanin-1, -2 and -3 Receptor Messenger RNAs in Central and Peripheral Rat Tissues," *Neuroscience* 95(1):265-271, 2000.

\* cited by examiner

GAL(1-15) AND ANALOGUES THEREOF FOR USE IN THE PREVENTION AND/OR TREATMENT OF ALCOHOL-RELATED EFFECTS AND DISORDERS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920198_401USPC_SEQUENCE_LISTING. The text file is 2.4 KB, was created on May 8, 2021, and is being submitted electronically via EFS-Web.

FIELD OF THE INVENTION

The present invention relates to the medical field, in particular to GAL(1-15) or to the analogues thereof, for use in the prevention and/or the treatment of alcohol-related effects and disorders, especially the use thereof to reduce alcohol consumption.

BACKGROUND OF THE INVENTION

Alcohol consumption is considered a major risk factor for disease and mortality worldwide according to the World Health Organization (2014). Current therapies in alcohol use disorders (AUD) have limited efficacy, produce several adverse effects and present high rates of relapse. In the absence of effective treatments, it is therefore of great importance to find new biological targets that could modulate alcohol consumption. Numerous neurotransmitters have been implicated in AUD including GABA, glutamate, dopamine, noradrenalin, serotonin, and several endogenous neuropeptides (Schneider et al., 2007; Marcinkiewcz et al., 2016).

Galanin (GAL) is a neuropeptide (Tatemoto et al., 1983) widely distributed in neurons within the central nervous system (CNS) (Jacobowitz et al., 2004). Three GAL receptor (GALR1-3) subtypes with high affinities for GAL have been cloned (Branchek et al., 2000; Mitsukawa et al., 2008). GALR1 and GALR3 mainly activate inhibitory G proteins Gi/Go, while GALR2 mainly couples to Gq/G11 to mediate excitatory signalling (Branchek et al., 2000).

GAL participates in a number of central functions modulating neuroendocrine levels, pain control, cardiovascular functions, food intake, and mood disorders (Mitsukawa et al., 2008; Diaz-Cabiale et al., 2010; Lang et al., 2015). GAL and its receptors are involved in drug abuse and addiction (Picciotto, 2008), including alcohol intake and alcoholism (Lewis et al., 2004; Lewis et al., 2005). Microinjection of GAL into the third ventricle increased ethanol consumption in Sprague-Dawley rats in a two-bottle choice test from 7% ethanol solution in water, and this increase was completely reversed with the GAL receptor antagonist M40 (Lewis et al., 2004). These effects of GAL on ethanol consumption were also found with injections of GAL directly into the paraventricular nucleus (PVN) of the hypothalamus (Rada et al., 2004). Moreover, mice overexpressing GAL show an increase in ethanol intake and preference in comparison with their wild-type peers (Karatayev et al., 2009), while GAL knockout mice drink less ethanol and decrease the preference for it (Karatayev et al., 2010). Not only the PVN, but also the reward circuitry seems to be involved in the effects of GAL promoting alcohol drinking. GAL may increase the release of dopamine in the nucleus accumbens (NAc) (Rada et al., 1998), and this effect would be consistent with the ability of GAL to increase the rewarding effects of alcohol (Picciotto et al., 2010).

In addition to GAL, N-terminal fragments known as GAL(1-15) are also active in the CNS (Hedlund et al., 1996; Diaz-Cabiale et al., 2005; Diaz-Cabiale et al., 2010; Millon et al., 2015; Millon et al., 2016; Flores-Burgess et al., 2017; Millon et al., 2017). Both GAL and GAL(1-15) molecules have specific roles in cardiovascular regulation and interact differently with other neuropeptides (Diaz-Cabiale et al., 2005). It has recently been described that GAL(1-15) induces strong depression-related and anxiogenic-like effects in rats, and these effects are significantly stronger than those induced by GAL. The GALR1/GALR2 heteroreceptor complexes in the dorsal hippocampus and especially in the dorsal raphe, areas rich in GAL(1-15) binding sites (Hedlund et al., 1992), were involved in these effects (Millon et al., 2015). The presence of binding sites specific for GAL(1-15) in the dorsal hippocampus, neocortex, and corpus striatum (Hedlund et al., 1992), which are part of the mesolimbic dopamine system (Koob, 1992), suggests a role of GAL(1-15) in circuits relating to the rewarding and motivational effects of drugs of abuse.

Now it has surprisingly been found that GAL(1-15) with the general formula:

Gly-Trp-Thr-Leu-Asn-Ser-Ala-Gly-Tyr-Leu-Leu-Gly-Pro-His-Ala(SEQ ID NO: 1), or

GWTLNSAGYLLGPHA (SEQ ID NO: 1), or the analogues thereof, or pharmaceutically acceptable salts, esters, tautomers, solvates, and hydrates thereof, can be used to prevent and/or treat alcohol-related effects and disorders, especially in regard to reducing alcohol consumption.

BRIEF DESCRIPTION OF THE INVENTION

Alcohol consumption is considered a major risk factor for disease and mortality worldwide. In the absence of effective treatments in alcohol use disorders (AUDs), it is important to find new biological targets that could modulate alcohol consumption. The role of GAL(1-15) in voluntary ethanol consumption was tested in rats using the two-bottle choice paradigm, and the effects of GAL(1-15) have been compared with the whole galanin molecule (GAL). The present invention describes the first time that GAL(1-15), via central mechanisms, induces a strong reduction in ethanol consumption and preference in rats. These effects were significantly different from GAL. Galanin receptor 2 (GALR2) was involved in said effects, because the specific GALR2 antagonist M871 blocked GAL(1-15) mediated actions in ethanol intake and preference. Importantly, the mechanism of this action involves changes in GALR expression and also in immediate-early gene C-Fos and the gene related to the internalisation of Rab5 receptors in the striatum. The relevance of the striatum as a target for GAL(1-15) was supported by the effect of GAL(1-15) on the locomotor activity of rats after ethanol administration. These results may give the basis for the development of novel therapeutics strategies using GAL(1-15) analogues for the treatment of AUDs in humans.

According to lo aforementioned, the present invention relates to the use, as indicated, of GAL(1-15) or an analogue thereof, or pharmaceutically acceptable salt, ester, tautomer, solvate, or hydrate thereof, for the prevention and/or treatvement of the alcohol-related disorders such as acute intoxication, harmful use, dependence syndrome, withdrawal state, and other mental and behavioural disorders induced by alcohol due to the consumption thereof. In particular, the present invention relates to the use of GAL(1-15) or an analogue thereof, or pharmaceutically acceptable salt, ester, tautomer, solvate, or hydrate thereof, suitable for reducing alcohol consumption.

DETAILED DESCRIPTION OF THE INVENTION

Figure 1:
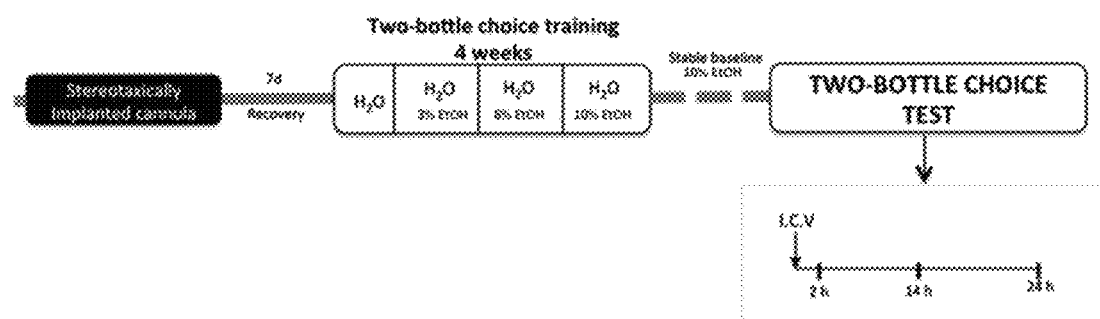
FIG. 1. Experimental design of voluntary ethanol intake.

In the present invention, the role of intracerebroventricular (i.c.v.) GAL(1-15) in voluntary ethanol consumption in rats has been assessed using the two-bottle choice paradigm, and the effects of GAL (1-15) have furthermore been compared with those of GAL. Moreover, the involvement of GALR2 in GAL(1-15)-mediated effects in this test was analysed with the selective GALR2 receptor antagonist M871. In order to investigate whether the effect of GAL(1-15) in voluntary ethanol consumption was associated with the reward circuit, the effect of GAL(1-15) in the expression of the early gene C-Fos, the gene related to the internalisation of Rab5, and GALR1 and GALR2 receptors, it is being studied in the corpus striatum. The effects of treatment with GAL(1-15) on locomotor activity induced by alcohol have therefore also been investigated.

The induction of a strong reduction in ethanol consumption and preference in rats by means of GAL(1-15), via central mechanisms, has been described herein for the first time. These effects were significantly different from those of GAL, which shows a differential role of GAL compared with GAL(1-15) in alcohol consumption-related behaviour. GALR2 was involved in these effects, since the specific GALR2 antagonist M871 blocked GAL(1-15)-mediated actions in ethanol intake and preference. Importantly, the mechanism of this action involves changes in the GAL receptor expression and also in immediate early gene C-Fos and the gene related to the internalisation of Rab5 receptors in the corpus striatum, an area rich in GAL fragment binding sites (Hedlund et al., 1992) and critical for the rewarding and motivational effects of drugs of abuse (Koob, 1992). The relevance of the corpus striatum as a target for GAL(1-15) was also supported by the effect of GAL(1-15) on the locomotor activity of rats after ethanol administration.

GAL(1-15) at the dose of 3 nmol induced a marked reduction in ethanol consumption and preference in the two-bottle choice test at 2 hours, which effect was maintained at 24 hours. Taking into account that this alcohol drinking paradigm by choosing between two bottles induces a voluntary intake of large quantities of alcohol (Simms et al., 2008), the present data suggests that GAL(1-15) may be used as a drug for treating AUD in humans.

It has previously been shown that GAL(1-15) increases anxiety-like and depressive-like behaviours in rats (Millon et al., 2015; Millon et al., 2017). Although emotional states such as anxiety are relevant variables to modulate alcohol-taking behaviour, increasing alcohol consumption and preference (Chappell et al., 2013), GAL(1-15)-mediated effects do not seem to involve emotional regulation since a reduction in alcohol intake and preference was observed.

In addition, a tentative explanation for the reduced alcohol intake induced by central GAL(1-15) administration is that GAL(1-15) by itself may induce aversion rather than attenuate the rewarding properties of alcohol. However, the selected doses of GAL(1-15) have no effect on food and water intake, which suggests that the reduced alcohol intake is not driven by an aversion to alcohol.

Since GAL(1-15) did not modify the food intake in rats that had been chronically consuming ethanol, it can also be suggested that in this model, the rats were not consuming ethanol just for its calories (Lewis et al., 2004).

Furthermore, the effects of GAL(1-15) in the two-bottle choice test were significantly different from the corresponding effects induced by GAL. In this model, a GAL 3 nmol dose had no effect with respect to the vehicle group in all the analysed parameters. In previous studies, GAL microinjected into the third ventricle increased the 7% ethanol intake in the two-bottle choice test (Lewis et al., 2004), and this increase was greater during the light phase, where the animals are inactive and normally drink very little (Lewis et al., 2004). The different results found in this work could be explained by the differences in percentage of ethanol and the light/dark cycle used, since a choice between 10% ethanol versus water was used, so the percentage of ethanol solution could affect the result of the test (Leeman et al., 2010; Tarragon et al., 2012). Furthermore, measurements were taken in the dark period, when rats are more active, while the ethanol intake produced by GAL was greater in the light period (Lewis et al., 2004).

However, because GAL(1-15) reduces ethanol consumption and preference, where GAL produces the opposite effect according to other authors, in the present invention the perspectives concerning the specific role of GAL(1-15) in ethanol intake are validated and expanded.

A different action of GAL and GAL(1-15) in behaviour functions has previously been described (Millon et al., 2017). GAL(1-15) induces strong anxiogenic-like and depression-related effects in rats, and these effects were significantly stronger than those induced by GAL (Millon et al., 2015). GAL(1-15) is also able to enhance the antidepressant effects induced by the 5HT1A receptor agonist 8-OH-DPAT in the forced swimming test, an effect that is again significantly stronger than that induced by GAL (Millon et al., 2016). The different action between GAL and GAL(1-15) was observed not only in behavioural functions, but also in central cardiovascular regulation (Diaz-Cabiale et al., 2005; Diaz-Cabiale et al., 2010). The results in relation to ethanol intake confirm a unique action of GAL(1-15) in brain communication.

The mechanism that explained the differences between GAL and GAL(1-15) is that the preferred N-terminal GAL fragment binding site is the result of the formation of GALR1/GALR2 heteromers highly specific for GAL fragments (Fuxe et al., 2008; Fuxe et al., 2012; Millon et al., 2015). The fact that GALR2 receptor antagonist M871 blocked the reduction in ethanol intake and preference induced by GAL(1-15) confirms that GAL(1-15) acts through heterodimer GALR1/GLR2 to reduce ethanol consumption and preference.

The GAL receptors involved in alcoholism are not well characterised; however, several studies indicate that GALR3 is involved in alcohol consumption (Belfer et al., 2007; Ash et al., 2011; Ash et al., 2014; Scheller et al., 2017). Because GALR3 is mainly restricted to the hypothalamus and pituitary (Smith et al., 1998; Waters et al., 2000), it has been proposed that said areas are crucial for this effect. The importance of GALR1 and GALR2 receptors in the reduction of ethanol consumption and preference induced by GAL(1-15) is demonstrated in the present invention, and it is suggested that the corpus striatum, a key region in the reward effects of drugs (Koob, 1992), is involved in GAL(1-15)-mediated effects. In this voluntary ethanol consumption model, GAL(1-15) induced a significant increase in C-Fos mRNA and Rab5 expression in the corpus striatum, which indicates an enhancement of neuronal activation and receptor internalisation in this area (Borroto-Escuela et al., 2012). Moreover, in these animals, after GAL(1-15) injection, a significant reduction in GALR1 expression and a slight decrease in GALR2 mRNA in the corpus striatum was observed, which suggests that both striatal receptors participated in the GAL(1-15)-mediated effects on voluntary ethanol intake in this nucleus. Interestingly, the evidence that ethanol injections in naïve animals have no effect on GALR1 and GALR2 expression in the corpus striatum indicates that ethanol per se does not influence GALR expression and confirms that the effects at GALR level in this model were induced by GAL(1-15).

The relevance of the corpus striatum as a target for GAL(1-15) was supported by the ability of GAL(1-15) to favour the suppression of locomotor activity induced by ethanol. Ethanol suppression of locomotor activity following ethanol i.p. injection is a well-known behavioural effect mainly mediated by the dopaminergic system, including the corpus striatum. Accordingly, it has been demonstrated that this effect is notably reduced when the dopaminergic system is injured using 6-OHDA, which produces rapid dopamine depletion in the corpus striatum (Breese et al., 1984). The present invention suggests that the potentiation of the hypolocomotion induced by GAL(1-15) in rats treated with alcohol may require modulation of the dopaminergic system through GAL(1-15), and it probably includes the corpus striatum because it is an important target of dopaminergic projections.

Although previously, the increase in the ethanol intake of GAL was related directly with several areas within the hypothalamus (Leibowitz et al., 2003; Rada et al., 2004; Schneider et al., 2007), the present invention suggests that GAL(1-15) acts through the corpus striatum, an area that has binding sites specific for GAL(1-15) (Hedlund et al., 1992). Involvement of the corpus striatum in GAL(1-15)-mediated action would explain the different action between GAL and GAL(1-15) in ethanol intake.

Dopamine should be considered a neurotransmitter target involved in the reduction of ethanol consumption by GAL(1-15). Supporting this hypothesis, GAL reduces behavioural response following treatment with several addictive substances, such as morphine or amphetamines, for example, mainly modulating dopaminergic neurotransmission (Tsuda et al., 1998; Pierce et al., 2006), and dopamine transmission plays a crucial role in the motor effects of alcohol in the corpus striatum (Brabant et al., 2014).

The results included in the present invention showed that GAL(1-15) reduces voluntary alcohol consumption; however, because a positive correlation has been demonstrated between taking alcohol and oral operant self-administration (Green and Grahame, 2008), GAL(1-15) can also be expected to reduce the self-administration of alcohol in rats. In fact, other neuropeptide-related drugs, such as ghrelin antagonists, reduced ethanol intake preference and ethanol operant self-administration (Gomez et al., 2015). Furthermore, not only has it been demonstrated that GAL(1-15) has biological functions, other galanin N-terminal fragments, such as GAL(1-16), have biological functions. Therefore, GAL(1-16) may substantially increase 5HT1A agonist binding sites Kd values in the ventral limbic cortex of the rat, without affecting Bmax values (Diaz-Cabiale et al., 2000); these results are consistent with other work where GAL(1-15) reduces 5HT1A receptor affinity in the dorsal hippocampus without affecting Bmax values (Hedlund et al., 1994). To that end, functional studies have demonstrated that several galanin N-terminal fragments seem to exert similar effects (Diaz-Cabiale et al., 2000).

In conclusion, the present invention indicates that GAL (1-15) induces a strong reduction in ethanol consumption and preference in rats, probably with the involvement of the corpus striatum, a key region in the reward effects of drugs, giving the basis for the development of novel therapeutic strategies using GAL(1-15) analogues for the treatment of AUDs in humans.

The present invention therefore provides:

The present invention relates to the use of GAL(1-15) or an analogue thereof, or pharmaceutically acceptable salt, ester, tautomer, solvate, or hydrate thereof, i.e., the compounds of the invention, to prevent and/or treat alcohol-related effects and disorders, especially by reducing alcohol consumption.

GAL(1-15) or the analogues thereof may be in their crystalline form as free compounds or as solvates. In this sense, as it is used herein the term "solvate" includes both pharmaceutically acceptable solvates, i.e., solvates that can be used to manufacture a medicinal product, and pharmaceutically unacceptable solvates, which may be useful in the preparation of pharmaceutically acceptable solvates or salts. The nature of the pharmaceutically acceptable solvate is not critical provided that it is pharmaceutically acceptable. In one embodiment in particular, the solvate is a hydrate. The solvates may be obtained by conventional solvation methods known to those persons skilled in the art.

For use in therapy, GAL(1-15) or analogues thereof, or salts, esters, tautomers, solvates, or hydrates thereof, would preferably be in a substantially pure or pharmaceutically acceptable form, i.e., with a pharmaceutically acceptable level of purity and excluding the usual pharmaceutical additives such as diluents and vehicles, and not including materials considered toxic at the usual dosage levels. The levels of purity for the active ingredient are preferably above 50%, more preferably above 70%, and even more preferably above 90%. In a preferred embodiment, levels are greater than 95% in GAL(1-15) or analogues thereof, or salts, esters, tautomers, solvates, or hydrates thereof.

The aforementioned alcohol-related disorders include acute intoxication, harmful use, dependence syndrome, withdrawal state, and other mental and behavioural disorders induced by alcohol due to the consumption thereof.

According to the International Classification of Diseases (ICD-10), mental and behavioural disorders due to use of alcohol (F10) are classified based on the use of a psychoactive substance (F10-F19) and include the following subsections: F10. Mental and behavioural disorders due to use of alcohol. F10.0. Acute intoxication. F10.1. Harmful use. F10.2. Dependence syndrome. F10.3. Withdrawal state. F10.4. Withdrawal state with delirium. F10.5. Psychotic disorder. F10.6. Amnesic syndrome. F10.7. Residual and late-onset psychotic disorder. F10.8. Other mental and behavioural disorders. F10.9. Unspecified mental and behavioural disorder.

Acute intoxication (F.10.0) is a transient condition following the administration of alcohol resulting in disturbances in level of consciousness, cognition, perception, affect, or behaviour, or other psychophysiological functions and responses.

Harmful use (F10.1) means a use which affects mental or physical health, without entirely meeting the dependence or any other criteria indicated in F10.

Dependence syndrome (F.10.2) is a set of physiological (somatic symptoms, tolerance), behavioural, and cognitive phenomena in which the use of the substance is the highest priority for the individual.

The withdrawal state (F10.3) is a set of somatic and psychological symptoms occurring on absolute or relative withdrawal of a substance after repeated and usually prolonged and/or high-dose, use of that substance. It is one of the indicators of the presence of dependence syndrome.

In one embodiment, the alcohol-related disorder is acute inebriation or pathological intoxication. Preferably, the effects related to acute inebriation or pathological intoxication include a sedating effect, lack of motor coordination, confusion, neurodegeneration, or any combinations thereof.

In another embodiment, the alcohol-related disorder is dependence syndrome or withdrawal state. Preferably, dependence syndrome- or withdrawal state-related effects include anxiety, depression, tremors, agitation and discomfort, emotional or cognitive impairment compounded by a negative mood, anhedonia or memory issues; tolerance or inability to control alcohol consumption; neuroinflammation, neurotoxicity, neuronal death, or any combinations thereof.

"Alcohol" is herein understood mainly but not exclusively as alcoholic drinks containing ethanol. It is also possible that other types of alcohols may cause the same symptoms after intake.

In one embodiment, the present invention relates to the use of GAL(1-15) or an analogue thereof, or pharmaceutically acceptable salt, ester, tautomer, solvate, or hydrate thereof for the preparation of a pharmaceutical composition to prevent and/or treat alcohol-related effects and disorders, especially by reducing alcohol consumption, as a pharmaceutical composition comprising GAL(1-15) or an analogue thereof, or pharmaceutically acceptable salt, ester, tautomer, solvate, or hydrate thereof. Preferably, said pharmaceutical composition consists of GAL(1-15) or an analogue thereof, or pharmaceutically acceptable salt, ester, tautomer, solvate, or hydrate thereof, although said pharmaceutical composition may optionally comprise pharmaceutically acceptable excipients or vehicles and/or diluents.

Finally, the present invention relates to a method for the prevention and/or treatment of alcohol-related effects and disorders, particularly to a method to reduce alcohol consumption, comprising the administration of GAL(1-15) or an analogue thereof, or pharmaceutically acceptable salt, ester, tautomer, solvate, or hydrate thereof, or a pharmaceutical composition comprising GAL(1-15) or an analogue thereof, or pharmaceutically acceptable salt, ester, tautomer, solvate, or hydrate thereof.

In one embodiment, the use is preventive and the administration of a compound of the invention, or a pharmaceutical composition comprising a compound of the invention, is carried out before the intake of alcohol or any of its derivatives. In another embodiment, the use is preventive and the administration of a compound of the invention, or a pharmaceutical composition comprising a compound of the invention, is performed during the intake of alcohol or any of its derivatives. In another embodiment, the use is for treatment and the administration of a compound of the invention, or a pharmaceutical composition comprising a compound of the invention, is performed during the intake of alcohol or of any of its derivatives. In another embodiment, the use is for treatment and the administration of a compound of the invention, or a pharmaceutical composition comprising a compound of the invention, is performed after the intake of alcohol or of any of its derivatives.

The compound of the invention, or a pharmaceutical composition comprising a compound of the invention, can be administered together with another active ingredient in a simultaneous or sequential combination.

To prepare the pharmaceutical compositions of this invention, a suitable amount of the active ingredient(s) in the form of a salt or in the form of a base is combined in an intimate mixture with a pharmaceutically acceptable vehicle, which may acquire a wide range of forms depending on the form of preparation desired for administration. These pharmaceutical compositions are desirably found in a unit dosage form suitable for nasal, oral, rectal, or percutaneous administration, or by means of parenteral injection. For example, when preparing compositions in oral dosage form, any of the usual pharmaceutical media may be used, such as, for example, water, glycols, oils, alcohols, and the like in case of oral liquid preparations such as suspensions, syrups, elixirs, and solutions; or solid vehicles such as starches, sugars, kaolin, lubricants, binders, disintegrants, and the like in the case of powders, pills, capsules, and tablets. Due to their ease of administration, tablets and capsules represent the most advantageous oral unit dosage form, in which case solid pharmaceutical vehicles are obviously used.

It is especially advantageous to formulate the aforementioned pharmaceutical compositions in unit dosage forms for easy administration and dose uniformity. As used in the specifications and claims, the unit dosage form refers to physically separated units suitable as unit dosages, wherein each unit contains a predetermined amount of active ingredient(s) calculated to produce the desired therapeutic effect in association with the necessary pharmaceutical vehicle. Examples of these unit dosage forms are tablets (including coated or scored tablets), capsules, pills, sachets of powders, wafers, injectable solutions or suspensions, teaspoons, tablespoons, and the like, and segregated multiples thereof.

The compound of the invention, or a pharmaceutical composition comprising a compound of the invention, can be administered before, during, or after the administration of the other active ingredient, preferably after the administration of the serotonin reuptake inhibitor, provided that the time between the administration of the compound of the invention, or the pharmaceutical composition comprising a compound of the invention, and the administration of the other active ingredient is such that the active ingredients are allowed to act synergistically in the CNS. When simultaneous administration is envisaged, a composition containing both the compound of the invention and the other active ingredient, may be particularly appropriate. Or the compound of the invention, or the pharmaceutical composition comprising a compound of the invention, and the other active ingredient, may be separately administered in the form of suitable compositions. The compositions may be prepared as described above.

The present invention also comprises products containing the compound of the invention, or the pharmaceutical composition comprising a compound of the invention, and the other active ingredient as a combination preparation for simultaneous, independent or sequential, separate use, or in the prevention or treatment of alcohol-related effects and disorders by especially reducing alcohol consumption. These products may comprise, for example, a kit comprising independent unit dosage forms containing the compound of the invention, or the pharmaceutical composition comprising a compound of the invention, and separate unit dosage forms containing the active ingredient, all contained in the same package or container, for example, in a blister.

As used in this invention, the term "active ingredient", "active substance", "substance or pharmaceutically active substance", or "pharmaceutically active ingredient" means any component which potentially provides a pharmacological effect or another type of effect on the diagnosis, cure, palliation, treatment, or prevention of a disease, or which affects the structure or function of the human body or the body of other animals. The term includes those components which promote a chemical change in the manufacture of the drug and are present therein in a modified form and envisaged to provide a specific activity or effect.

The aforementioned invention is further described in detail in the following non-limiting and merely illustrative examples.

EXAMPLES

Materials and Methods

Animals

Male Sprague—Dawley rats (body weight 225-250 g, age 8 weeks) were obtained from Criffa and maintained in a humidity-controlled and temperature-controlled (20-22° C.) room. The rats in the two-bottle choice paradigm were during the entire protocol maintained on a 12-hour reversed light/dark cycle (lights off at 10 am) whereas the other rats were kept on 12-hour light/dark cycle. The animals had free access to food pellets and tap water. All animal experimentation was conducted in accordance with the University of Malaga Guidelines for the Care and Use of Laboratory Animals.

Intracerebroventricular Injections

This protocol has been used previously (Diaz-Cabiale et al., 2011; Millon et al., 2015). Briefly, the rats were anaesthetised intraperitoneally with Equitesin (3.3 ml/kg body weight) and stereotaxically implanted with a unilateral chronic 22-gauge stainless steel guide cannula into the right lateral cerebral ventricle using the following coordinates: 1.4 mm lateral and 1 mm posterior to bregma and 3.6 mm below the surface of the skull (Paxinos, 1986). After surgery, animals were individually housed and allowed a recovery period of 7 days. The injections in the lateral ventricle were performed using a 26-gauge stainless steel injection cannula connected via PE-10 tubing to a Hamilton syringe. The total volume was 5 µl per injection, and the infusion time was 1 minute.

The solutions were prepared freshly, and the peptides were dissolved in artificial cerebrospinal fluid (with a composition of 120 nM NaCl, 20 nM NaH$_2$CO$_3$, 2 nM KCl, 0.5 nM KH$_2$PO$_4$, 1.2 nM CaCl$_2$, 1.8 nM MgCl$_2$, 0.5 nM Na$_2$SO$_4$, and 5.8 nM D-glucose, pH 7.4). GAL was obtained from NeoMPS, Strasbourg, France; GAL(1-15) and the GALR2 receptor antagonist M871 were obtained from Tocris Bioscience, Bristol, UK.

Two-Bottle Choice Test for Voluntary Ethanol Consumption and Preference

The two-bottle choice test was used to determine the voluntary ethanol consumption of rats as described previously (Castilla-Ortega et al., 2016). Briefly, after 7 days of water consumption (both bottles), a choice between water and increasing concentrations of ethanol [3, 6, and 10% (v/v)] was offered for 7 days each. A choice between 10% ethanol (v/v) and water was offered for several days until reaching a stable baseline value. Water and ethanol consumption were recorded daily. The position of the bottles was changed every day to avoid preference for location. Water intake (g/kg), ethanol intake (g/kg), and preference ([ethanol consumption/total fluid [water plus ethanol] consumption×100]) were calculated for each animal. Throughout the experiment, evaporation and spillage estimates were calculated using an empty cage with two bottles, one containing water and the other containing the appropriate ethanol solution. In the experiments, a choice between ethanol (10%) and water was offered.

Three sets of experiments were conducted in the two bottle choice paradigm. In the first set of experiments, a dose-response curve of GAL(1-15) was performed. For this, groups of rats received i.c.v. 1 nmol or 3 nmol of GAL(1-15), or vehicle 2, 14, and 24 hours before the measurements. In the second set of experiments, the effects of the two-bottle choice test for GAL and GAL(1-15) were compared. For this, groups of rats received i.c.v. 3 nmol of GAL, 3 nmol of GAL(1-15), or vehicle, 2, 14, and 24 hours before the test. In the last set of experiments, the role of GALR2 was studied; for this, groups of rats received i.c.v. 3 nmol of GAL(1-15) combined with 3 nmol of GALR2 2 antagonist M871 hours before the measurements.

The general scheme of the experimental design is shown in FIG. 1.

mRNA expression of galanin receptors, C-Fos and Rab5 genes in the corpus striatum during voluntary ethanol consumption.

Groups of rats from the two-bottle choice paradigm were killed by decapitation 2 hours after a single i.c.v. administration of 3 nmol of GAL(1-15) or vehicle, and the corpus striatum was dissected and frozen on solid $CO_2$ until mRNA expression analysis.

RNA Isolation and Quantitative Real-Time PCR Analysis

The method to perform RNA isolation and RT-PCR was described previously (Millon et al., 2015). Total RNA was isolated from the corpus striatum using RNeasy Lipid Tissue kit (Qiagen, Hilden, Germany). cDNA was obtained using a Reverse Transcriptase Core kit (Eurogentec, Seraing, Belgium). These steps were performed according to the manufacturer's instructions.

All PCR analyses were performed in triplicate using Power SYBR Green PCR Master Mix (Applied Biosystems, Foster City, USA) in the 7500 RT-PCR system (Applied Biosystems, Foster City, USA). The primer sequences used in this study are:

```
GAPDH-Forward:
                                    (SEQ ID NO: 2)
5'-GCTCTCTGCTCCTCCCTGTTC;

GAPDH-Reverse:
                                    (SEQ ID NO: 3)
5'-GAGGCTGGCACTGCACAA;

GALR1-Forward:
                                    (SEQ ID NO: 4)
5'-AAAACTGGACAAAACTTAGCC;

GALR1-Reverse:
                                    (SEQ ID NO: 5)
5'-GGATACCTTTGTCTTTGCTC;

GALR2-Forward:
                                    (SEQ ID NO: 6)
5'-AACAGGAATCCACAGACC;

GALR2-Reverse:
                                    (SEQ ID NO: 7)
5'-CCCTTTGGTCCTTTAACAAG;

C-FOS-Forward:
                                    (SEQ ID NO: 8)
5'-AAACGGAGAATCCGAAGG;

C-FOS-Reverse:
                                    (SEQ ID NO: 9)
5'-CGTCTTCAAGTTGATCTGTC;

RAB5-Forward:
                                    (SEQ ID NO: 10)
5'-AAAAGAGCTGTTGACTTCC;

RAB5-Reverse:
                                    (SEQ ID NO: 11)
5'-AGGTCTACTCCTCTTCCTC.
```

The data was analysed using the comparative Ct method and normalised to measurements of glyceraldehyde-3-phosphate dehydrogenase (GAPDH) mRNA.

Alcohol Dehydrogenase Enzyme Assay

The activity of hepatic cytosolic alcohol dehydrogenase (ADH) in the rats from the two-bottle choice test was analysed. ADH activity has a good correlation with ethanol elimination rates in vivo (Lumeng et al., 1979) and chronic ethanol administration causes an increase in ADH activity (Buris et al., 1985).

The livers were removed 2 hours after i.c.v. injections and frozen in solid $CO_2$ until use. Determination of ADH activity was performed in homogenized liver tissue in a TrisHCl solution (10 mM, pH=8.8; 0.5 mM dithiothreitol) centrifuged at 12.000 g for 10 minutes. ADH activity was evaluated using a microassay adapted to Cobas Mira analyser according to Shephard and colleagues (Shephard et al., 1987). Briefly, 300 µl of NAD solution (2.9 mM in 0.1 M Glycine/NaOH: p=10) was added to 30 µl of sample. The first optical reading was recorded before the addition of 20 µl of 17 mM ethanol, and then the rate of change in absorption of the NADH chromogen was recorded at 340 nm over time on the Cobas Mira analyser at 37° C. One activity unit was defined as the reduction of 1 mol NAD to NADH/min at 37° C.

Locomotor Activity Experiments

In this experiment, the effects of GAL(1-15) (3 nmol) on ethanol-reduced locomotion (1.75 g/kg; intraperitoneal (i.p.)) (Vallof et al., 2016) were investigated. Locomotor activity was recorded in rat open field (100×100×50 cm) where animals were individually placed and left to freely explore. Their behaviour was recorded over a 30-minute period by ceiling-mounted video camera, and locomotor activity was analysed using the video-tracking software EthovisionXT. After each assay, all surfaces were cleaned with a paper towel and 70% ethanol solution. For locomotor activity, total distance travelled (cm) and mean speed (cm/s) were recorded. Groups of rats were administered via i.c.v. GAL(1-15) or vehicle 20 minutes before the test; i.p. ethanol (1.75 g/kg) or saline solution administration was performed 5 minutes before the test.

GALR1 and GALR2 mRNA Expression after Acute Administration of Ethanol

Groups of naïve rats were injected i.p. with ethanol at 4 g/kg (Bilbao et al., 2016), dissolved in a 0.9% sterile saline solution (w/v), and 0, 2, and 4 hours after the injection the brains were extracted after a rapid decapitation. The corpus striatum was quickly extracted from all the animals and frozen immediately on solid $CO_2$ until use. The method to perform RNA isolation and RT-PCR was described previously.

Ethanol Self-Administration

Figure 7:
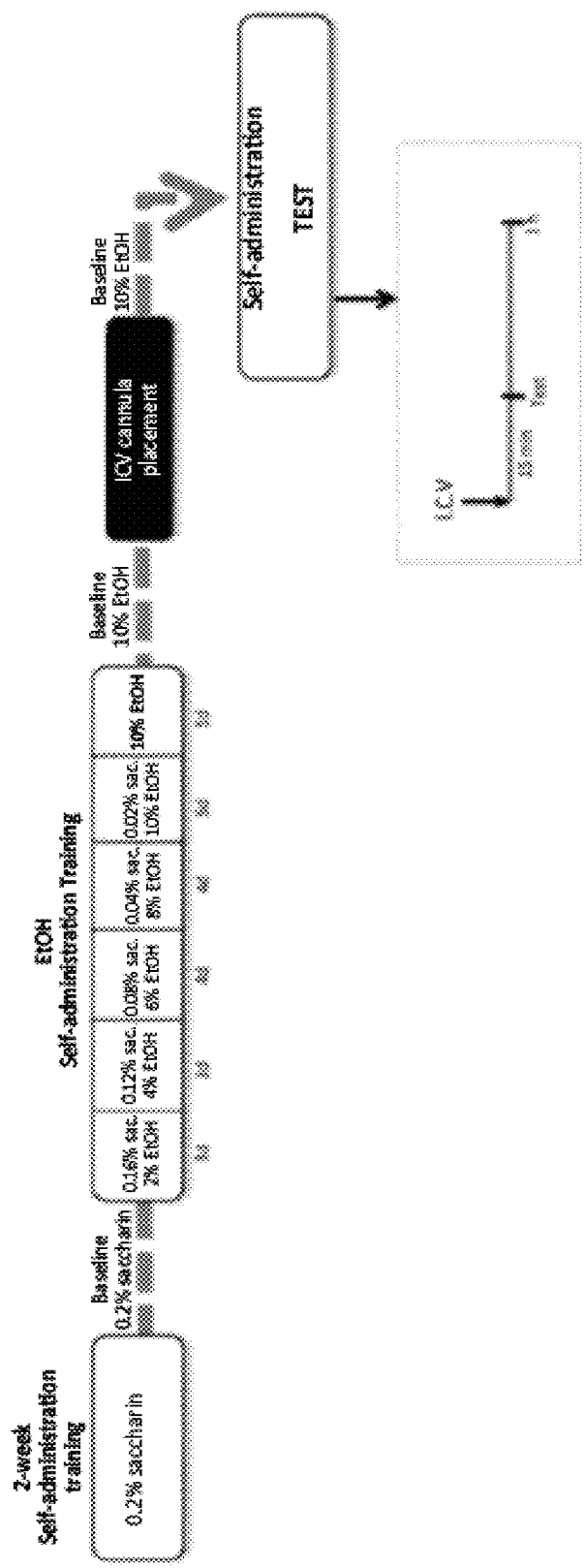
FIG. 7. Experimental design of ethanol self-administration. i.c.v., intracerebroventricular.

The use of operant models as substance self-administration models are widely used for performing motivation or hedonic studies. In these models, the animal has to "work" to obtain the reinforcing substance by pressing a lever, which allows the investigator to observe the animal's interest in the substance, as well as to learn the effect of the substance as a reward for the animal (Leeman et al., 2010). The method is performed according to earlier protocols (Alén et al., 2009) with some modifications. The test consists of a two-week training phase in which rats are kept the first 2 to 4 days with a water restriction to facilitate the learning of the task of pressing the lever to obtain the reinforcement. Animals are exposed daily to 30-minute sessions in self-administration boxes (Letica instruments). The boxes are equipped with two retractable levers located on both sides of a liquid dispenser (0.1 mL) positioned in the centre of the box panel. The levers are programmed to act as an active or inactive lever, with the active lever providing as a reward 0.1 mL of 0.2% sodium saccharin solution, in the first training phase, following a Fixed Ratio 1 (FR-1). Once the training period is over, where all the animals have proven to have learned the task, daily sessions continue to be performed until establishing a stable baseline. Then training begins for ethanol consumption, and for this purpose a gradual increase in ethanol concentration (from 2% to 10%) is performed at the same time as a gradual reduction in saccharin concentration (from 0.16% to 0%) over several days, where after this period the animals become accustomed consuming 10% ethanol. After several sessions to establish a stable baseline, the animals are subjected to placement of a chronic intracerebroventricular cannula, leaving them for several days after this intervention to again establish a stable ethanol consumption baseline. Then the test is performed, consisting of a 30-minute session after administration of the different treatments, recording the number of active lever presses, as well as the number of rewards (FIG. 7).

Two sets of ethanol self-administration experiments were performed. In the first set of experiments, a dose-response curve of GAL(1-15) was performed. For this, groups of rats received i.c.v. GAL(1-15) at doses of 0.3, 1, and 3 nmol, or vehicle. In the second set of experiments, the effect of GAL 3 nmol and GAL(1-15) 3 nmol in ethanol self-administration were compared.

Statistical Analysis

The data is presented as the means±standard error of the mean, and sample numbers (n) are indicated in figure legends. All data was analysed using GraphPad PRISM 4.0 (GraphPad software). For comparing two experimental conditions, Student's unpaired t-test statistical analyses were performed. Otherwise, one-way analyses of variance (ANOVAs) or two-way ANOVAs followed by Fisher's LSD comparison post-tests were performed. Differences were considered significant with $p<0.05$ (*$p<0.05$; $p<0.01$; *$p<0.001$).

Example 1. Liver ADH Activity in Voluntary Ethanol Consumption

Voluntary ethanol intake through the two-bottle choice test protocol induced a significant increase in ADH activity compared with the baseline group ($t_{11}=3.281$ $p<0.01$), which confirmed the validity of this model (Table 1).

TABLE 1

Animal liver ADH activity in the two-bottle choice paradigm. Effects of the voluntary ethanol intake in animals in the two-bottle choice test on liver ADH activity. Cerebrospinal fluid-injected rats were used as the vehicle group, and naïve rats were used as the baseline group. Data represents mean ± SEM (n = 6-7 animals per group).

| Treatment | ADH activity | |
|---|---|---|
| | Baseline value | Vehicle/EtOH |
| ADH (protein IU/g) | 251.4 ± 14.8 | 313.1 ± 10.6** |

**$p < 0.01$ versus baseline group according to the Student's t-test.

Figure 2:
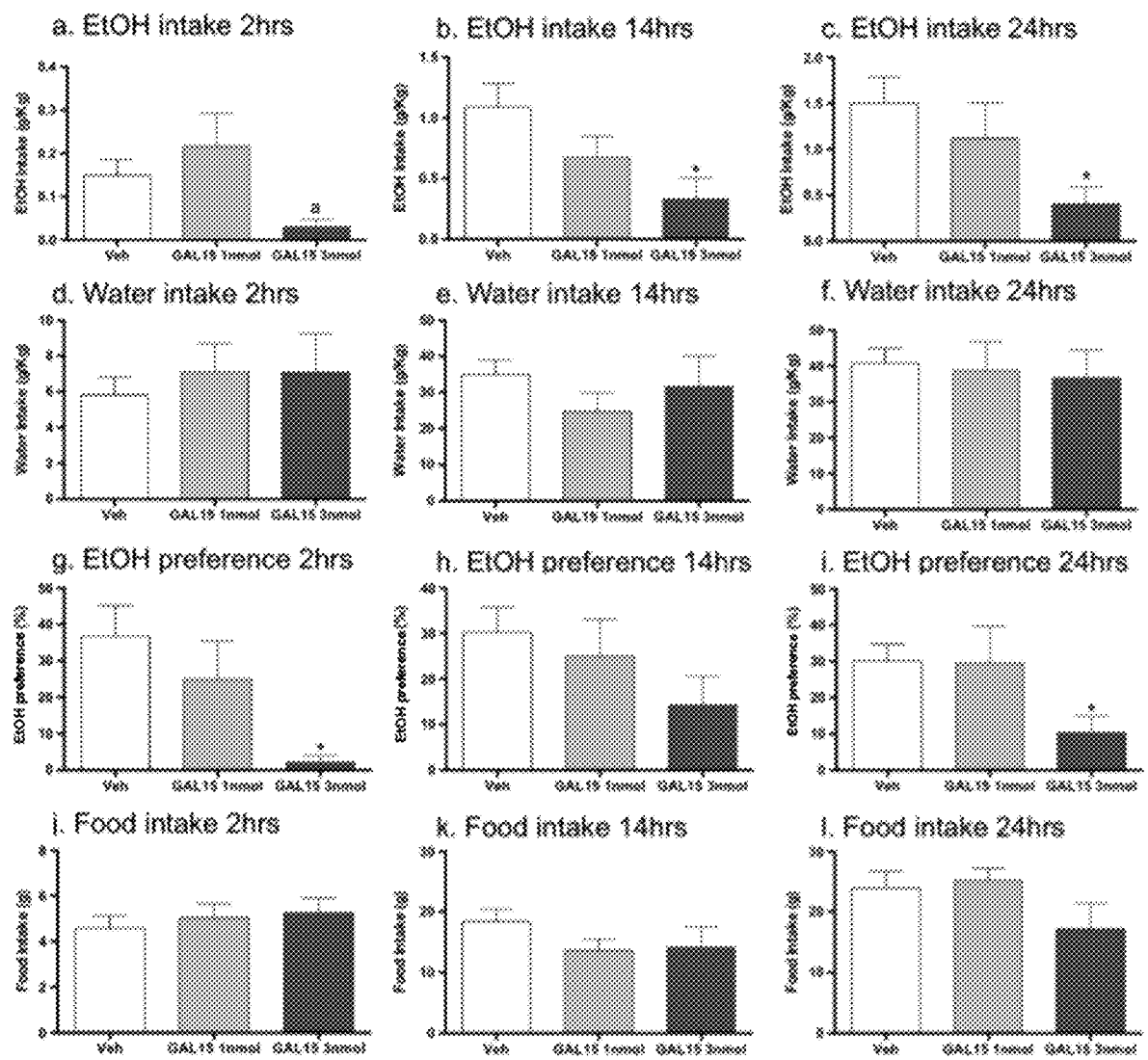
FIG. 2. Dose-response curve of galanin (1-15) [GAL15] in the two-bottle choice paradigm with 10% ethanol (EtOH) concentration in rats. GAL15 (at 1 or 3 nmol/rat) was administered i.c.v. 2, 14, and 24 hours before the measurements. Cerebrospinal fluid-injected rats were used as the vehicle group. Vertical bars represent mean±SEM (n=6-18 animals per group) of EtOH intake (g/kg; a, b, c), water intake (g/kg; d, e, f), preference for EtOH (%; g, h, i), and food intake (g; j, k, l) during the different periods. (a) $^a$p<0.05 versus rest of the groups (rest of graphs) *p<0.05 versus vehicle group according to one-way ANOVA followed by Fisher's LSD test.

Example 2. GAL(1-15) Induced a Decrease in Ethanol Intake and Alcohol Preference in the Two-Bottle Choice Paradigm GAL(1-15) at 3 nmol significantly decreased ethanol intake at 2 hours (one-way ANOVA, F2.30=3.54 $p<0.05$, Fisher's LSD post hoc test: $p<0.05$; FIG. 2a), at 14 hours (one-way ANOVA, F2.30=3.44 $p<0.05$, Fisher's LSD post hoc test: $p<0.05$; FIG. 2b) and at 24 hours (one-way ANOVA, F2.29=3.59 $p<0.05$, Fisher's LSD post hoc test: $p<0.05$; FIG. 2c) after administration. GAL(1-15) at a dose of 1 nmol had no effect on ethanol intake in all the time points analysed.

Additionally, 2 hours after the i.c.v. administration of 3 nmol of GAL(1-15), a significant decrease by 90% in the preference for ethanol was observed (one-way ANOVA, F2.31=3.46 $p<0.05$, Fisher's LSD post hoc test: $p<0.05$; FIG. 2g). This effect was maintained for 24 hours (one-way ANOVA, F2.31=3.57 $p<0.05$, Fisher's LSD post hoc test: $p<0.05$; FIG. 2i). Again, the dose of 1 nmol of GAL(1-15) had no effects on preference for ethanol.

In the water intake (FIG. 2d, e, f) and food intake (FIG. 2j, k, l), no differences were found at any time point after i.c.v. administration of GAL(1-15) at any dose.

These results indicate that GAL(1-15) causes a strong decrease in alcohol intake and preference in rats.

Example 3. Comparison Between GAL and GAL(1-15) in the Two-Bottle Choice Paradigm In ethanol intake, the overall one-way ANOVA showed a significant difference between GAL and the N-terminal GAL(1-15) fragment at 2, 14, and 24 hours after treatments. Two hours after the injection, GAL(1-15) significantly decreased ethanol intake compared with GAL (one-way ANOVA, F2.31=4.208 $p<0.05$, Fisher's LSD post hoc test: $p<0.01$; FIG. 3a). The same response pattern was observed at the other time points, GAL(1-15) significantly decreased ethanol intake versus GAL groups 14 (one-way ANOVA, F2.30=3.97 $p<0.05$, Fisher's LSD post hoc test: $p<0.05$; FIG. 3b) and 24 hours (one-way ANOVA, F2.30=2.53 $p<0.05$, Fisher's LSD post hoc test: $p<0.05$; FIG. 3c) after i.c.v. injection.

In regard to preference for ethanol, the difference between GAL and GAL(1-15) was observed again. GAL(1-15) decreased preference for ethanol compared with GAL 2 hours after administration (one-way ANOVA, F2.30=3.55 $p<0.05$, Fisher's LSD post hoc test: $p<0.05$; FIG. 3g), an effect that was maintained 24 hours later (one-way ANOVA, F2.32=3.43 $p<0.05$, Fisher's LSD post hoc test: $p<0.05$; FIG. 3i).

Figure 3:
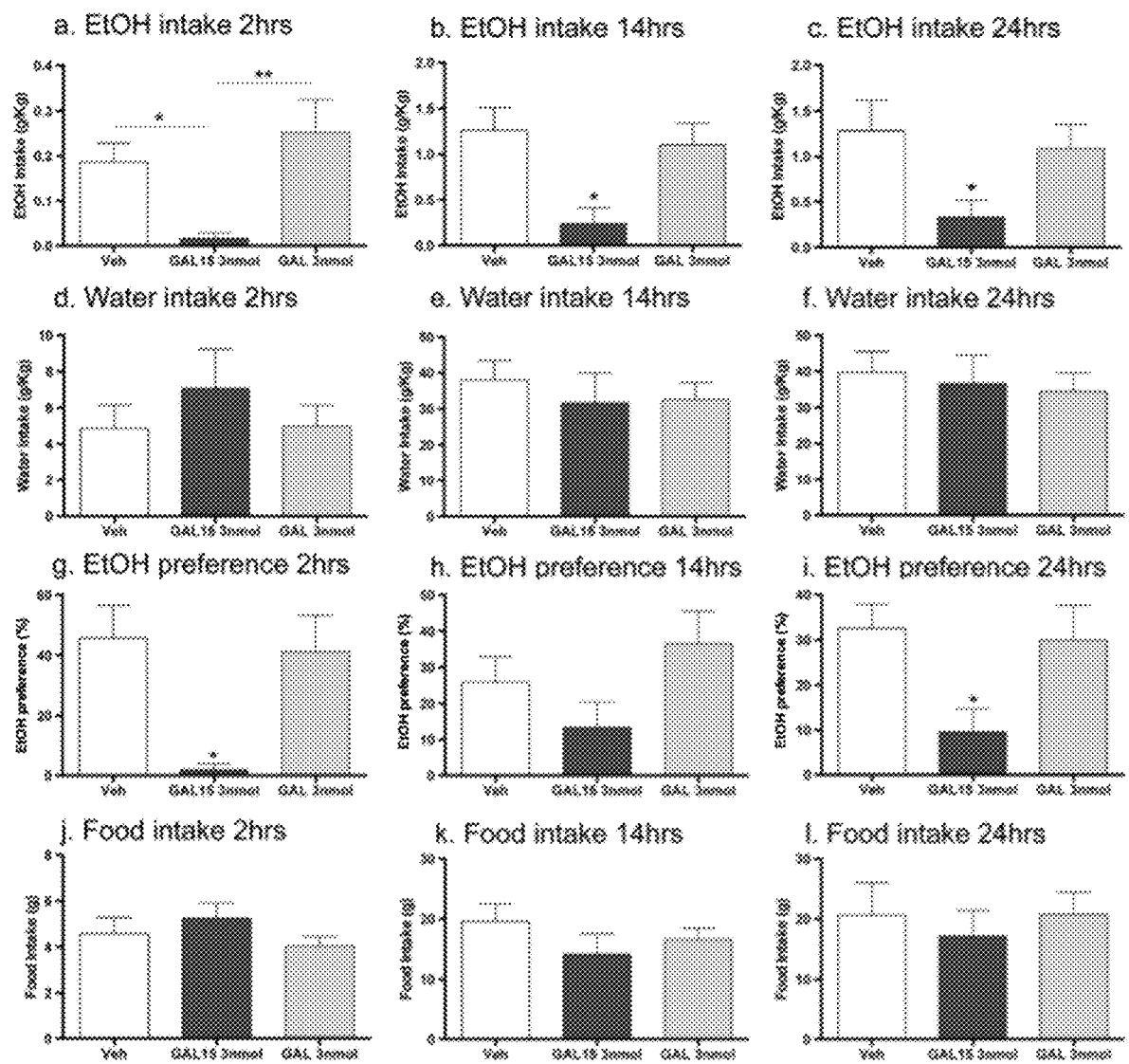
FIG. 3. Effect of administration of galanin (GAL) and galanin (1-15) [GAL15] in the two-bottle choice paradigm with 10% ethanol (EtOH) concentration in rats. GAL (3 nmol/rat) and GAL15 (3 nmol/rat) were administered i.c.v. 2, 14, and 24 hours before the measurements. Cerebrospinal fluid-injected rats were used as the vehicle group. Vertical bars represent mean±SEM (n=7-15 animals per group) of EtOH intake (g/kg; a, b, c), water intake (g/kg; d, e, f), preference for EtOH (%; g, h, i), and food intake (g; j, k, l) during the different periods. (a) *p<0.05 versus vehicle **p<0.01 versus GAL15 3 nmol group (rest of graphs) *p<0.05 versus rest of the groups according to one-way ANOVA followed by Fisher's LSD test.

GAL has no effect on ethanol intake and preference compared with the vehicle at any time point (FIG. 3).

No differences were found between GAL and the GAL (1-15) fragment in water intake (FIG. 3d, e, f) or in food intake (FIG. 3j, k, l).

Figure 4:
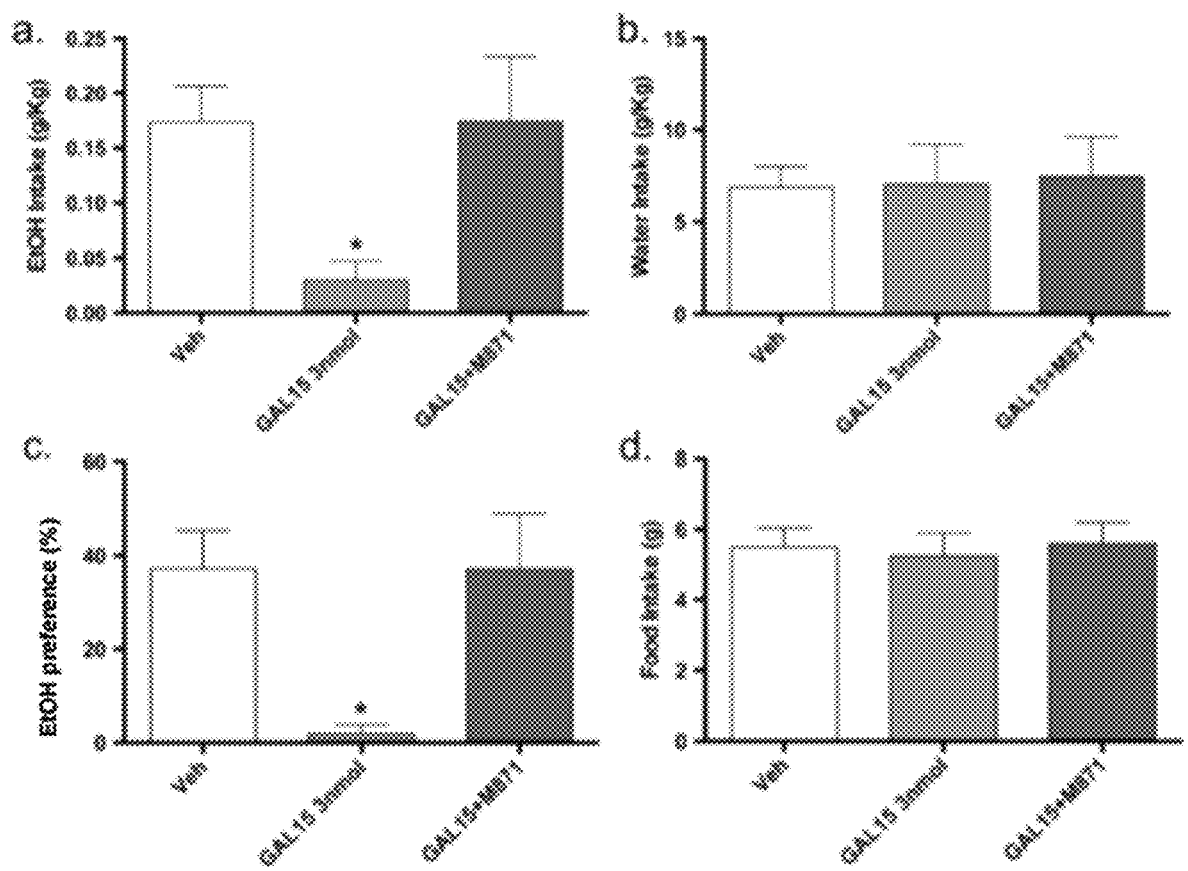
FIG. 4. Effects of co-administration of the GALR2 receptor antagonist M871 (3 nmol/rat) and galanin (1-15) [GAL15] in the two-bottle choice paradigm with 10% ethanol (EtOH) concentration in rats. The treatments were injected i.c.v. 2 hours before the measurements. Cerebrospinal fluid-injected rats were used as the vehicle group. Vertical bars represent mean±SEM (n=7-21 animals per group) of (a) EtOH intake (g/kg), (b) water intake (g/kg), (c) preference for EtOH (%), and (d) food intake (g) during the different periods. *p<0.05 versus rest of the groups according to one-way ANOVA followed by Fisher's LSD test.

Example 4. GAL(1-15)-Mediated Effects Blocked by the GALR2 Receptor Antagonist M871 in the Two-Bottle Choice Paradigm In the two-bottle choice test, the GALR2 antagonist M871 significantly blocked the decrease in ethanol intake (one-way ANOVA, F2.34=3.72 p<0.05, Fisher's LSD post hoc test: p<0.05; FIG. 4a) induced by GAL(1-15) 2 hours after administration.

In regard to preference for ethanol, the same type of change was observed. Thus, GALR2 participated in the GAL(1-15)-mediated effect, because GALR2 antagonist M871 significantly blocked the decrease in preference for ethanol induced by GAL(1-15) (one-way ANOVA, F2.32=3.39 p<0.05, Fisher's LSD post hoc test: p<0.05; FIG. 4c).

GALR2 antagonist M871 alone at the dose of 3 nmol had no effect on ethanol intake (0.13±0.06 g/kg) or on preference for ethanol (12.65±8.23%).

Neither water intake (FIG. 4b) nor food intake (FIG. 4d) were modified with M871 (water intake: 8.26±2.00 g/kg; food intake: 6.67±0.95 g) or GAL(1-15)+M871 2 hours after injection.

Figure 5:
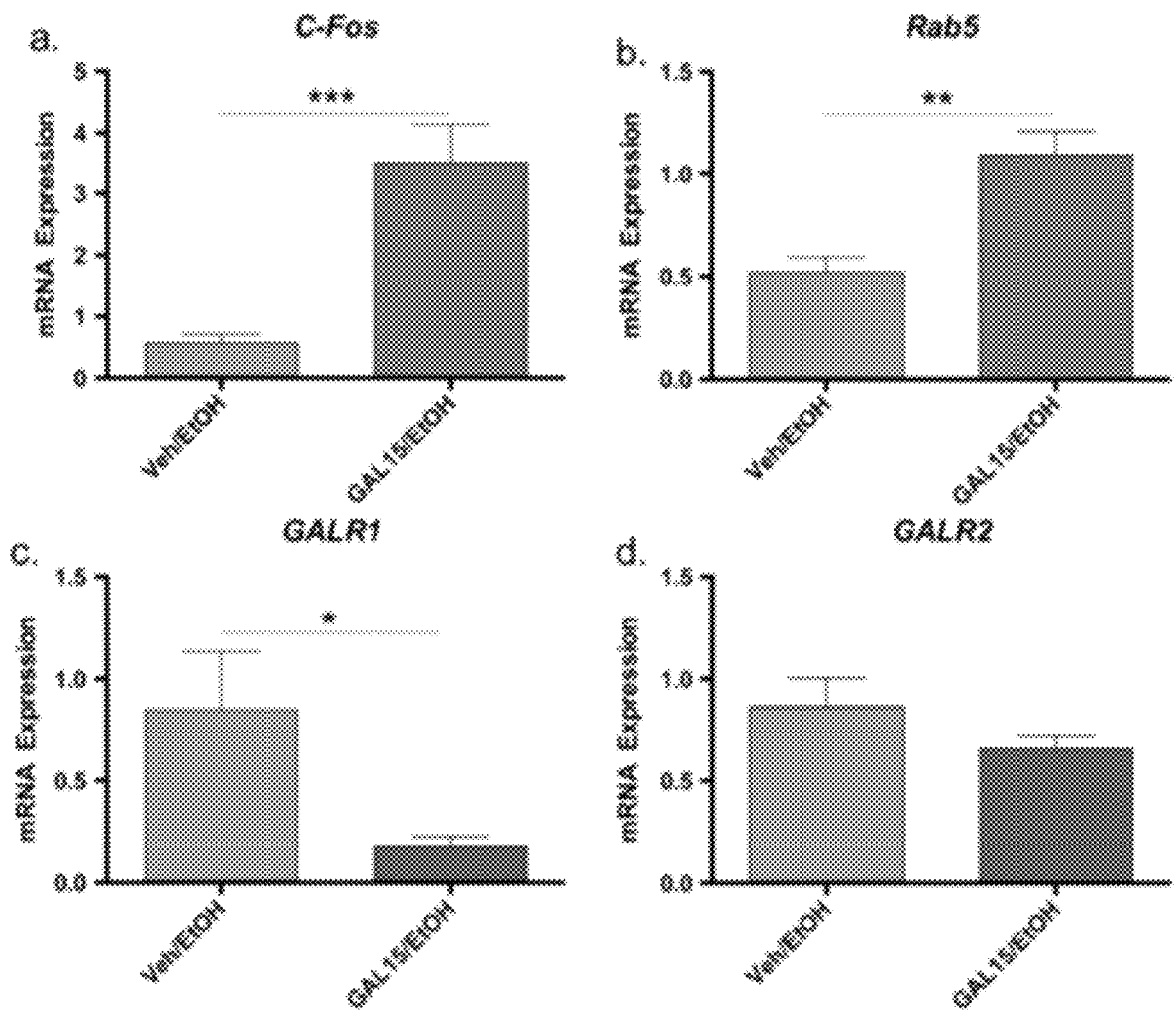
FIG. 5. Effects of galanin (1-15) [GAL15] in corpus striatum mRNA expression of C-Fos (a), Rab5 (b), GALR1 (c), and GALR2 (d) in the two-bottle choice paradigm exposed rats. GAL15 was injected i.c.v. 2 hours before the measurements. Cerebrospinal fluid-injected rats were used as the vehicle group. Vertical bars represent mean±SEM (n=5-6 animals per group). *p<0.05; p<0.01; *p<0.001 versus vehicle/EtOH group according to Student's t-test.

Example 5. Effects of GAL(1-15) on Galanin Receptor mRNA Expression and on C-Fos and Rab5 Genes in the Corpus Striatum in Voluntary Ethanol Consumption As shown in FIG. 5, GAL(1-15) at the dose of 3 nmol produced a significant increase in mRNA levels of C-Fos ($t_8$=5.488 p<0.001; FIG. 5a) and Rab5 ($t_6$=4.148 p<0.01; FIG. 5b) genes in the two-bottle choice test 2 hours after administration.

The administration of GAL(1-15) also modified GALR1 and GALR2 receptor expression in the corpus striatum, which produced a significant decrease in GALR1 mRNA levels ($t_{10}$=2.341 p<0.05; FIG. 5c), and a slight reduction in GALR2 expression ($t_{10}$=1.360 p=0.101; FIG. 5d), suggesting the involvement of both receptors in the effects of GAL(1-15).

Example 6. Effects of GAL(1-15) on Ethanol-Reduced Locomotion

Figure 6:
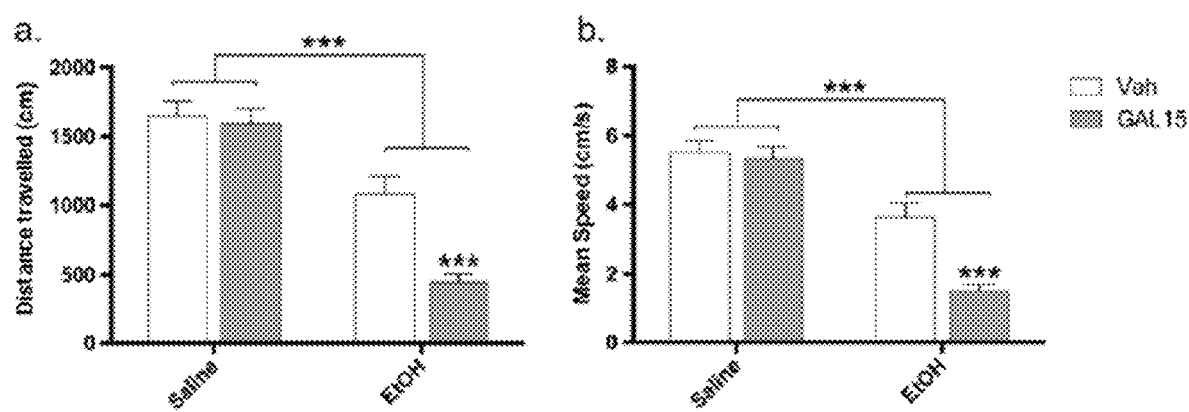
FIG. 6. Effects of galanin 1-15 [GAL15] in ethanol-induced locomotor modification in rats. GAL 15 (3 nmol; i.c.v.) was injected 20 minutes before the test, and acute injection ethanol (1.75 g/kg; i.p.) was administered 5 minutes before the test. Data represents mean±SEM (n=6-8 animals per group) of total distance travelled (a) and mean speed (b) in open field during the 5-minute test period. ***p<0.001 according to two-way ANOVA followed by Fisher's LSD test.

As previously described, the i.p. administration of ethanol at 1.75 g/kg reduced the distance travelled (one-way ANOVA, F1.25=62.2 p<0.001) and mean speed (one-way ANOVA, F1.25=62.2 p<0.001) five minutes after administration (FIG. 6).

The effect of the dose of 3 nmol of GAL(1-15) on locomotion (distance travelled and mean speed), was dependent on i.p. ethanol (distance travelled: two-way ANOVA for alcohol/i.c.v. treatment interaction; F1.25=7.19 p<0.01; mean speed: two-way ANOVA for alcohol/i.c.v. treatment interaction; F1.25=7.19 p<0.01) (FIG. 6). Therefore, in rats following i.p. administration of ethanol, GAL(1-15) decreased the distance travelled (Fisher's LSD post hoc test: p<0.001; FIG. 6a), whereas no such effects were observed in rats with systemic administration of saline solution (Fisher's LSD post hoc test: p=0.71; FIG. 6a). Similar to the distance travelled, GAL(1-15) decreased mean speed only in rats systemically treated with ethanol (Fisher's LSD test: p<0.001; FIG. 6b).

Example 7. GALR1 and GALR2 Expression in the Corpus Striatum after the Acute Administration of Ethanol To determine whether ethanol influenced GALR1 and GALR2 expression in the corpus striatum, the effects of the acute administration of ethanol on GALR1 and GALR2 mRNA levels in the corpus striatum at 2 and 4 hours are evaluated.

As shown in Table 2, a single injection of ethanol (4 g/kg i.p.) had no effect on GALR1 expression in the corpus striatum at 2 and 4 hours after administration (one-way ANOVA, F2.14=1.19 p=0.24).

TABLE 2

Effects of ethanol administration on GALR1 and GALR2 expression in the corpus striatum. The effects of acute i.p. administration of EtOH (4 g/kg) on GALR1 and GALR2 mRNA expression in the corpus striatum were measured at 0, 2, and 4 hours after injection. Data represents mean ± SEM (n = 4-8 animals per group). No significant differences were found by one-way ANOVA.

| mRNA expression | Time after i.p. injection of EtOH (4 g/kg) | | |
|---|---|---|---|
| | 0 hours | 2 hours | 4 hours |
| GALR1 | 0.87 ± 0.2 | 0.60 ± 0.1 | 0.47 ± 0.1 |
| GALR2 | 1.21 ± 0.1 | 1.23 ± 0.1 | 1.44 ± 0.1 |

No effects were observed on GALR2 mRNA levels at any time point (one-way ANOVA, F2.14=1.15 p=0.34) either.

Example 8. Ethanol Self-Administration

Figure 8:
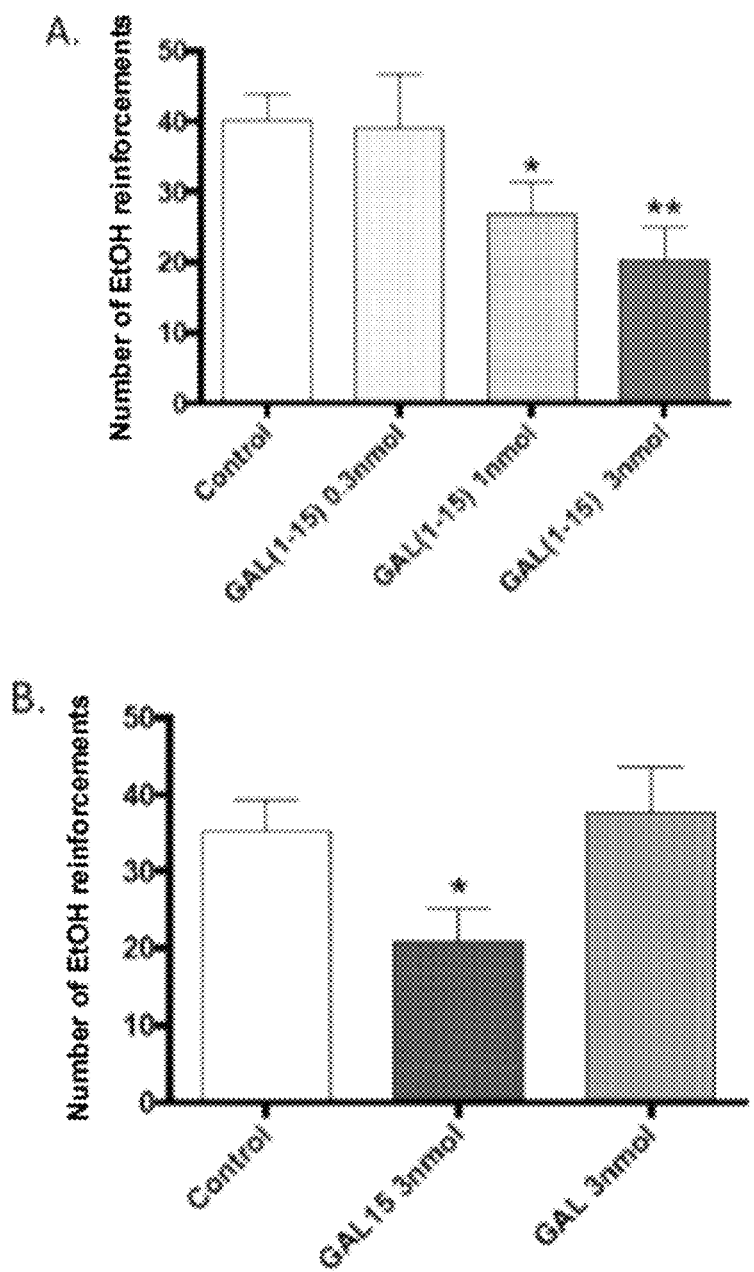
FIG. 8. Role of GAL(1-15) in the operant model of ethanol self-administration in rats. (A) Dose-response curve of GAL(1-15) in ethanol self-administration. GAL(1-15) (n=9-11 animals) was administered intracerebroventricularly (i.c.v.) 15 min before the test. Artificial cerebrospinal fluid was used as a control group. (B) Effect of the administration of GAL and GAL(1-15) in ethanol self-administration. GAL (3 nmol/rat) and GAL(1-15) (3 nmol/rat; n=9-13 animals) were injected i.c.v. 15 min before the test. Artificial cerebrospinal fluid was used with the control group. Vertical bars represent mean±standard error of the mean number of EtOH reinforcements during the test. *p<0.05 and **p<0.01 versus control group (A) and versus rest of the groups (B) according to one-way ANOVA followed by Fisher's post-test.

The administration of GAL(1-15) induced a significant decrease in motivation produced by ethanol consumption in rats. GAL(1-15) 1 nmol induced a significant decrease (p<0.05) in the number of ethanol reinforcements, with this reduction being even more pronounced with the GAL(1-15) dose of 3 nmol (p<0.01) (FIG. 8A). The administration of GAL(1-15) 0.3 nmol has no effect on the number of reinforcements in ethanol self-administration.

The statistical analysis performed using one-way ANOVA shows a significant difference between the N-terminal GAL (1-15) fragment and the whole GAL molecule in ethanol self-administration. Thus, GAL(1-15) 3 nmol injection significantly reduces the number of ethanol reinforcements compared with GAL (p<0.05) (FIG. 8B).

Operant self-administration models are used widely to study of motivated behaviour (Ettemberg review, 2009; Sanchis-Segura and Spanagel, 2006); GAL(1-15) induces a strong reduction in the number of reinforcements in ethanol self-administration, suggesting that GAL(1-15) induces a loss in alcohol-induced motivational conduct. These results obtained are consistent with previously obtained data, where GAL(1-15) produces a strong reduction in voluntary alcohol consumption and in preference for this drug (Millon et al., 2017), accentuating interest in the use of GAL(1-15) as a therapeutic strategy for the treatment of alcoholism.

Furthermore, the observed effect of GAL(1-15) in ethanol self-administration was significantly different from the effect produced by the whole GAL molecule. A differential role of GAL(1-15) compared to GAL in different behavioural functions was previously described (Millón et al., 2015; Millón et al., 2016; Millón et al., 2017). Thus, GAL(1-15) induces depression-related and anxiogenic-like effects in rats, and these effects were significantly stronger than those induced by GAL (Millón et al., 2015). Moreover, as previously mentioned, GAL(1-15) produces a reduction in alcohol consumption and in preference in a voluntary alcohol consumption model, showing a completely different role from what the whole GAL molecule has (Millón et al., 2017). The differential action between GAL and GAL(1-15) has been observed not only in behavioural functions, but also in central cardiovascular regulation (Diaz-Cabiale et al., 2005; Diaz-Cabiale et al., 2010). Therefore, the present results widely confirm a specific role of GAL(1-15) in cerebral communication.

In conclusion, the results indicate that GAL(1-15) produces a significant loss of motivation for alcohol consumption, being consistent with earlier data observed, where GAL(1-15) significantly decreases voluntary alcohol consumption and preference.

REFERENCES

Ash B L, Zanatta S D, Williams S J, Lawrence A J, Djouma E (2011). The galanin-3 receptor antagonist, SNAP 37889, reduces operant responding for ethanol in alcohol-preferring rats. *Regul Pept* 166: 59-67.

Ash B L, Quach T, Williams S J, Lawrence A J, Djouma E (2014). Galanin-3 receptor antagonism by SNAP 37889 reduces motivation to self-administer alcohol and attenuates cue-induced reinstatement of alcohol-seeking in iP rats. *Journal of pharmacological sciences* 125: 211-216.

Belfer I, Hipp H, Bollettino A, McKnight C, Evans C, Virkkunen M, et al. (2007). Alcoholism is associated with GALR3 but not two other galanin receptor genes. *Genes, brain, and behavior* 6: 473-481.

Bilbao A, Serrano A, Cippitelli A, Pavon F J, Giuffrida A, Suarez J, et al. (2016). Role of the satiety factor oleoylethanolamide in alcoholism. *Addiction biology* 21: 859-872.

Borroto-Escuela D O, Romero-Fernandez W, Mudo G, Perez-Alea M, Ciruela F, Tarakanov A O, et al. (2012). Fibroblast growth factor receptor 1-5-hydroxytryptamine 1A heteroreceptor complexes and their enhancement of hippocampal plasticity. *Biol Psychiatry* 71: 84-91.

Brabant C, Guarnieri D J, Quertemont E (2014). Stimulant and motivational effects of alcohol: lessons from rodent and primate models. *Pharmacol Biochem Behav* 122: 37-52.

Branchek T A, Smith K E, Gerald C, Walker M W (2000). Galanin receptor subtypes. *Trends Pharmacol Sci* 21: 109-117.

Breese G R, Baumeister A A, McCown T J, Emerick S G, Frye G D, Crotty K, et al. (1984). Behavioral differences between neonatal and adult 6-hydroxydopamine-treated rats to dopamine agonists: relevance to neurological symptoms in clinical syndromes with reduced brain dopamine. *J Pharmacol Exp Ther* 231: 343-354.

Burls L, Csabai G, Fodor M, Varga M (1985). Increase of alcohol dehydrogenase and protein content of liver following chronic ethanol administration. *FEBS Lett* 183: 143-144.

Castilla-Ortega E, Pavon F J, Sanchez-Marin L, Estivill-Torrus G, Pedraza C, Blanco E, et al. (2016). Both genetic deletion and pharmacological blockade of lysophosphatidic acid LPA1 receptor results in increased alcohol consumption. *Neuropharmacology* 103: 92-103.

Chappell A M, Carter E, McCool B A, Weiner J L (2013). Adolescent rearing conditions influence the relationship between initial anxiety-like behavior and ethanol drinking in male Long Evans rats. *Alcohol Clin Exp Res* 37 Suppl 1: E394-403.

Diaz-Cabiale Z, Parrado C, Vela C, Razani H, Covenas R, Fuxe K, et al. (2005). Role of galanin and galanin(1-15) on central cardiovascular control. *Neuropeptides* 39: 185-190.

Diaz-Cabiale Z, Parrado C, Narvaez M, Millon C, Puigcerver A, Fuxe K, et al. (2010). Neurochemical modulation of central cardiovascular control: the integrative role of galanin. *EXS* 102: 113-131.

Diaz-Cabiale Z, Parrado C, Narvaez M, Puigcerver A, Millon C, Santin L, et al. (2011). Galanin receptor/Neuropeptide Y receptor interactions in the dorsal raphe nucleus of the rat. *Neuropharmacology* 61: 80-86.

Flores-Burgess A, Millon C, Gago B, Narvaez M, Borroto-Escuela D O, Mengod G, et al. (2017). Galanin (1-15) enhancement of the behavioral effects of Fluoxetine in the forced swimming test gives a new therapeutic strategy against depression. *Neuropharmacology* 118: 233-241.

Fuxe K, Borroto-Escuela D O, Romero-Fernandez W, Tarakanov A O, Calvo F, Garriga P, et al. (2012). On the existence and function of galanin receptor heteromers in the central nervous system. *Front Endocrinol (Lausanne)* 3: 127.

Fuxe K, Marcellino D, Rivera A, Diaz-Cabiale Z, Filip M, Gago B, et al. (2008). Receptor-receptor interactions within receptor mosaics. Impact on neuropsychopharmacology. *Brain Res Rev* 58: 415-452.

Hedlund P B, Fuxe K (1996). Galanin and 5-HT1A receptor interactions as an integrative mechanism in 5-HT neurotransmission in the brain. *Ann N Y Acad Sci* 780: 193-212.

Hedlund P B, Yanaihara N, Fuxe K (1992). Evidence for specific N-terminal galanin fragment binding sites in the rat brain. *Eur J Pharmacol* 224: 203-205.

Jacobowitz D M, Kresse A, Skofitsch G (2004). Galanin in the brain: chemoarchitectonics and brain cartography—a historical review. *Peptides* 25: 433-464.

Karatayev O, Baylan J, Leibowitz S F (2009). Increased intake of ethanol and dietary fat in galanin overexpressing mice. *Alcohol* 43: 571-580.

Karatayev O, Baylan J, Weed V, Chang S, Wynick D, Leibowitz S F (2010). Galanin knockout mice show disturbances in ethanol consumption and expression of hypothalamic peptides that stimulate ethanol intake. *Alcohol Clin Exp Res* 34: 72-80.

Koob G F (1992). Drugs of abuse: anatomy, pharmacology and function of reward pathways. *Trends Pharmacol Sci* 13: 177-184.

Lang R, Gundlach A L, Holmes F E, Hobson S A, Wynick D, Hokfelt T, et al. (2015). Physiology, signaling, and pharmacology of galanin peptides and receptors: three decades of emerging diversity. *Pharmacological reviews* 67: 118-175.

Leeman R F, Heilig M, Cunningham C L, Stephens D N, Duka T, O'Malley S S (2010). Ethanol consumption: how should we measure it? Achieving consilience between human and animal phenotypes. *Addiction biology* 15: 109-124.

Leibowitz S F, Avena N M, Chang G Q, Karatayev O, Chau D T, Hoebel B G (2003). Ethanol intake increases galanin mRNA in the hypothalamus and withdrawal decreases it. *Physiol Behav* 79: 103-111.

Lewis M J, Johnson D F, Waldman D, Leibowitz S F, Hoebel B G (2004). Galanin microinjection in the third ventricle increases voluntary ethanol intake. *Alcohol Clin Exp Res* 28: 1822-1828.

Lewis M J, Rada P, Johnson D F, Avena N M, Leibowitz S F, Hoebel B G (2005). Galanin and alcohol dependence: neurobehavioral research. *Neuropeptides* 39: 317-321.

Lumeng L, Bosron W F, Li T K (1979). Quantitative correlation of ethanol elimination rates in vivo with liver alcohol dehydrogenase activities in fed, fasted and food-restricted rats. *Biochem Pharmacol* 28: 1547-1551.

Marcinkiewcz C A, Lowery-Gionta E G, Kash T L (2016). Serotonin's Complex Role in Alcoholism: Implications for Treatment and Future Research. *Alcohol Clin Exp Res* 40: 1192-1201.

Millon C, Flores-Burgess A, Narvaez M, Borroto-Escuela D O, Santin L, Parrado C, et al. (2015). A role for galanin N-terminal fragment (1-15) in anxiety- and depression-related behaviors in rats. *Int J Neuropsychopharmacol* 18: 1-13.

Millon C, Flores-Burgess A, Narvaez M, Borroto-Escuela D O, Santin L, Gago B, et al. (2016). Galanin (1-15) enhances the antidepressant effects of the 5-HT1A receptor agonist 8-OH-DPAT: involvement of the raphe-hippocampal 5-HT neuron system. *Brain Struct Funct.*

Millon C, Flores-Burgess A, Narvaez M, Borroto-Escuela D O, Gago B, Santin L, et al. (2017). The neuropeptides Galanin and Galanin(1-15) in depression-like behaviours. *Neuropeptides.*

Mitsukawa K, Lu X, Bartfai T (2008). Galanin, galanin receptors and drug targets. *Cell Mol Life Sci* 65: 1796-1805.

Paxinos G (1986). *The rat Brain in the stereotaxic coodinates*. New York: Academic Press edn.

Picciotto M R (2008). Galanin and addiction. *Cell Mol Life Sci* 65: 1872-1879.

Picciotto M R, Brabant C, Einstein E B, Kamens H M, Neugebauer N M (2010). Effects of galanin on monoaminergic systems and HPA axis: Potential mechanisms underlying the effects of galanin on addiction- and stress-related behaviors. *Brain Res* 1314: 206-218.

Pierce R C, Kumaresan V (2006). The mesolimbic dopamine system: the final common pathway for the reinforcing effect of drugs of abuse? *Neurosci Biobehav Rev* 30: 215-238.

Rada P, Mark G P, Hoebel B G (1998). Galanin in the hypothalamus raises dopamine and lowers acetylcholine release in the nucleus accumbens: a possible mechanism for hypothalamic initiation of feeding behavior. *Brain Res* 798: 1-6.

Rada P, Avena N M, Leibowitz S F, Hoebel B G (2004). Ethanol intake is increased by injection of galanin in the paraventricular nucleus and reduced by a galanin antagonist. *Alcohol* 33: 91-97.

Scheller K J, Williams S J, Lawrence A J, Djouma E (2017). The galanin-3 receptor antagonist, SNAP 37889, suppresses alcohol drinking and morphine self-administration in mice. *Neuropharmacology* 118: 1-12.

Schneider E R, Rada P, Darby R D, Leibowitz S F, Hoebel B G (2007). Orexigenic peptides and alcohol intake: differential effects of orexin, galanin, and ghrelin. *Alcohol Clin Exp Res* 31: 1858-1865.

Shephard M D, Penberthy L A, Berry M N (1987). Adaptation of methods for glutamate dehydrogenase and alcohol dehydrogenase activities to a centrifugal analyser: assessment of their clinical use in anoxic states of the liver. *J Clin Pathol* 40: 1240-1246.

Simms J A, Steensland P, Medina B, Abernathy K E, Chandler L J, Wise R, et al. (2008). Intermittent access to 20% ethanol induces high ethanol consumption in Long-Evans and Wistar rats. *Alcohol Clin Exp Res* 32: 1816-1823.

Smith K E, Walker M W, Artymyshyn R, Bard J, Borowsky B, Tamm J A, et al. (1998). Cloned human and rat galanin GALR3 receptors. Pharmacology and activation of G-protein inwardly rectifying K+ channels. *J Biol Chem* 273: 23321-23326.

Tarragon E, Balino P, Aragon C M, Pastor R (2012). Ethanol drinking-in-the-dark facilitates behavioral sensitization to ethanol in C57BL/6J, BALB/cByJ, but not in mu-opioid receptor deficient CXBK mice. *Pharmacol Biochem Behav* 101: 14-23.

Tatemoto K, Rokaeus A, Jornvall H, McDonald T J, Mutt V (1983). Galanin—a novel biologically active peptide from porcine intestine. *FEBS Lett* 164: 124-128.

Tsuda K, Tsuda S, Nishio I, Masuyama Y, Goldstein M (1998). Effects of galanin on dopamine release in the central nervous system of normotensive and spontaneously hypertensive rats. *American journal of hypertension* 11: 1475-1479.

Vallof D, Ulenius L, Egecioglu E, Engel J A, Jerlhag E (2016). Central administration of the anorexigenic peptide neuromedin U decreases alcohol intake and attenuates alcohol-induced reward in rodents. *Addiction biology.*

Waters S M, Krause J E (2000). Distribution of galanin-1, -2 and -3 receptor messenger RNAs in central and peripheral rat tissues. *Neuroscience* 95: 265-271.

The invention claimed is:

1. A method for prevention or treatment, or both, of alcohol-related effects and disorders in a subject in need thereof, comprising administering to the subject galanin(1-15) compound consisting of Gly-Trp-Thr-Leu-Asn-Ser-Ala-Gly-Tyr-Leu-Leu-Gly-Pro-His-Ala (GWTLNSAGYLLGPHA) (SEQ ID NO: 1), or a pharmaceutically acceptable salt thereof.

2. The method according to claim 1, wherein said method is for reducing alcohol consumption.

3. The method according to claim 1, wherein the alcohol-related effect or disorder is selected from the group consisting of acute intoxication, harmful use, dependence syndrome, withdrawal state, and mental or behavioural alcohol-induced disorders due to consumption thereof.

4. The method according to claim 1, wherein the alcohol-related effect or disorder is dependence syndrome or a withdrawal state.

5. A method for reducing alcohol consumption in a subject in need thereof, comprising administering to the subject a galanin(1-15) compound comprising Gly-Trp-Thr-Leu-Asn-Ser-Ala-Gly-Tyr-Leu-Leu-Gly-Pro-His-Ala (GWTLNSAGYLLGPHA) (SEQ ID NO: 1), or a pharmaceutically acceptable salt thereof.

* * * * *

SEQUENCE LISTING

<160> NUMBER OF SEQ ID NOS: 11

<210> SEQ ID NO 1
<211> LENGTH: 15
<212> TYPE: PRT
<213> ORGANISM: Unknown
<220> FEATURE:
<223> OTHER INFORMATION: General formula for GAL 1-15

<400> SEQUENCE: 1

Gly Trp Thr Leu Asn Ser Ala Gly Tyr Leu Leu Gly Pro His Ala
1               5                   10                  15

<210> SEQ ID NO 2

```
<211> LENGTH: 21
<212> TYPE: DNA
<213> ORGANISM: Artificial Sequence
<220> FEATURE:
<223> OTHER INFORMATION: GAPDH-Forward primer

<400> SEQUENCE: 2
gctctctgct cctccctgtt c                                              21

<210> SEQ ID NO 3
<211> LENGTH: 18
<212> TYPE: DNA
<213> ORGANISM: Artificial Sequence
<220> FEATURE:
<223> OTHER INFORMATION: GAPDH-Reverse primer

<400> SEQUENCE: 3
gaggctggca ctgcacaa                                                  18

<210> SEQ ID NO 4
<211> LENGTH: 21
<212> TYPE: DNA
<213> ORGANISM: Artificial Sequence
<220> FEATURE:
<223> OTHER INFORMATION: GALR1-Forward primer

<400> SEQUENCE: 4
aaaactggac aaaacttagc c                                              21

<210> SEQ ID NO 5
<211> LENGTH: 20
<212> TYPE: DNA
<213> ORGANISM: Artificial Sequence
<220> FEATURE:
<223> OTHER INFORMATION: GALR1-Reverse primer

<400> SEQUENCE: 5 ggatacctttt gtctttgctc                                               20

<210> SEQ ID NO 6
<211> LENGTH: 18
<212> TYPE: DNA
<213> ORGANISM: Artificial Sequence
<220> FEATURE:
<223> OTHER INFORMATION: GALR2-Forward primer

<400> SEQUENCE: 6
aacaggaatc cacagacc                                                  18

<210> SEQ ID NO 7
<211> LENGTH: 20
<212> TYPE: DNA
<213> ORGANISM: Artificial Sequence
<220> FEATURE:
<223> OTHER INFORMATION: GALR2-Reverse primer

<400> SEQUENCE: 7 cccttttggtc ctttaacaag                                               20

<210> SEQ ID NO 8
<211> LENGTH: 18
<212> TYPE: DNA
<213> ORGANISM: Artificial Sequence
<220> FEATURE:
<223> OTHER INFORMATION: C-FOS-Forward primer

<400> SEQUENCE: 8
```

```
aaacggagaa tccgaagg                                                   18

<210> SEQ ID NO 9
<211> LENGTH: 20
<212> TYPE: DNA
<213> ORGANISM: Artificial Sequence
<220> FEATURE:
<223> OTHER INFORMATION: C-FOS-Reverse primer

<400> SEQUENCE: 9
cgtcttcaag ttgatctgtc                                                 20

<210> SEQ ID NO 10
<211> LENGTH: 19
<212> TYPE: DNA
<213> ORGANISM: Artificial Sequence
<220> FEATURE:
<223> OTHER INFORMATION: RAB5-Forward primer

<400> SEQUENCE: 10
aaaagagctg ttgacttcc                                                  19

<210> SEQ ID NO 11
<211> LENGTH: 19
<212> TYPE: DNA
<213> ORGANISM: Artificial Sequence
<220> FEATURE:
<223> OTHER INFORMATION: RAB5-Reverse primer

<400> SEQUENCE: 11
aggtctactc ctcttcctc                                                  19
```